(12) United States Patent
Boitnott et al.

(10) Patent No.: US 9,618,436 B2
(45) Date of Patent: Apr. 11, 2017

(54) AUTOMATIC IMPULSE HAMMER FOR CHARACTERIZATION OF MECHANICAL PROPERTIES OF A MATERIAL

(71) Applicant: New England Research, Inc., White River Jct., VT (US)

(72) Inventors: Gregory Naff Boitnott, Hanover, NH (US); Gilles Yves Albert Bussod, Woodstock, VT (US); Jean-Carlo McLure, Wilder, VT (US)

(73) Assignee: New England Research, Inc., White River Jct., VT (US)

( * ) Notice: Subject to any disclaimer, the term of this patent is extended or adjusted under 35 U.S.C. 154(b) by 240 days.

(21) Appl. No.: 14/183,605

(22) Filed: Feb. 19, 2014

(65) Prior Publication Data

US 2014/0245819 A1    Sep. 4, 2014

Related U.S. Application Data

(60) Provisional application No. 61/851,087, filed on Mar. 1, 2013.

(51) Int. Cl.
  *G01N 3/40* (2006.01)
  *G01N 3/54* (2006.01)

(52) U.S. Cl.
  CPC .......... *G01N 3/40* (2013.01); *G01N 3/54* (2013.01); *G01N 2203/0039* (2013.01); *G01N 2203/0082* (2013.01)

(58) Field of Classification Search
  CPC .. G01N 3/42; G01N 3/48; G01N 3/40; G01N 2203/0082; G01N 3/54; G01N 2203/0039

USPC .............................................................. 73/82
See application file for complete search history.

(56) References Cited

U.S. PATENT DOCUMENTS

| | | | | |
|---|---|---|---|---|
| 4,848,141 A * | 7/1989 | Oliver | ............... | G01N 3/405 73/81 |
| 5,454,264 A * | 10/1995 | Lampinen | ............... | G01N 3/303 73/12.04 |
| 6,205,862 B1 * | 3/2001 | Nakamura | ............... | G01N 3/00 73/796 |
| 6,247,355 B1 * | 6/2001 | Suresh | ............... | G01N 3/42 73/82 |
| 6,718,820 B2 * | 4/2004 | Kwon | ............... | G01N 3/48 73/81 |
| 6,925,858 B2 * | 8/2005 | Miles | ............... | G01N 3/303 73/12.06 |
| 7,681,432 B2 * | 3/2010 | Hay | ............... | B82Y 35/00 73/1.79 |

(Continued)

*Primary Examiner* — Freddie Kirkland, III
(74) *Attorney, Agent, or Firm* — Richard A. Fagin

(57) ABSTRACT

A method for determining mechanical properties of a material includes positioning a probe tip of selected material properties having a selected geometry and a selected accelerating mass at a selected position and a selected height above a sample of the material. The probe tip is released to accelerate toward the sample. A first parameter related to force on the probe tip with respect to time is recorded. The releasing the probe tip is repeated with at least one of a different selected probe tip material, a different tip geometry, a different height and a different accelerating mass to record a second parameter related to force. The first and second parameters are used to determine at least one of an elastic property and a strength of the material.

17 Claims, 7 Drawing Sheets

(56) References Cited

U.S. PATENT DOCUMENTS 8,393,200 B2 * 3/2013 Scherzinger ............ G01N 3/42
73/81
2003/0140684 A1 * 7/2003 Broz ..................... G01N 3/48
73/81

* cited by examiner

AUTOMATIC IMPULSE HAMMER FOR CHARACTERIZATION OF MECHANICAL PROPERTIES OF A MATERIAL

CROSS-REFERENCE TO RELATED APPLICATIONS

Priority is claimed from U.S. Provisional Application No. 61/851,087 filed Mar. 1, 2013 and incorporated herein by reference in its entirety.

STATEMENT REGARDING FEDERALLY SPONSORED RESEARCH OR DEVELOPMENT

Not applicable.

BACKGROUND

This disclosure is related to the field of determining mechanical properties of a material and apparatus for making measurements for determining such properties. More specifically, the disclosure relates to automated apparatus that can make measurements corresponding to mechanical properties of materials using multiple values of measurement parameters to derive the mechanical properties.

A method known in the art for hardness measurement of a material sample is called "rebound hardness" where a projectile accelerated into a material sample and is bounced off the material sample. The projectile's energy loss during impact is used to produce a "hardness" index.

There are a number of devices known in the art to measure rebound hardness and at least one such device has been used to produce hardness profiles in rock core.

A related technique (indentation hardness) has been automated and integrated into an X-Y gantry system to map hardness variations in a material. Indentation hardness could be considered a simple version of a cone penetrometer. Indentation hardness measuring devices known in the art work on the principle that damage (inelastic deformation) to the material sample is produced by making the measurement, and that the amount of damage is used to determine a hardness index.

SUMMARY

A method according to one aspect for determining mechanical properties of a material includes positioning a probe tip of selected material properties having a selected geometry and a selected accelerating mass at a selected position and a selected height above a sample of the material. The probe tip is released to accelerate toward the sample. A first parameter related to force on the probe tip with respect to time is recorded. The releasing the probe tip is repeated with at least one of a different selected probe tip material, a different tip geometry, a different height and a different accelerating mass to record a second parameter related to force. The first and second parameters are used to determine at least one of an elastic property and a strength of the material.

Other aspects and advantages will be apparent from the description and claims that follow.

DETAILED DESCRIPTION

Figures 1A, 1B:
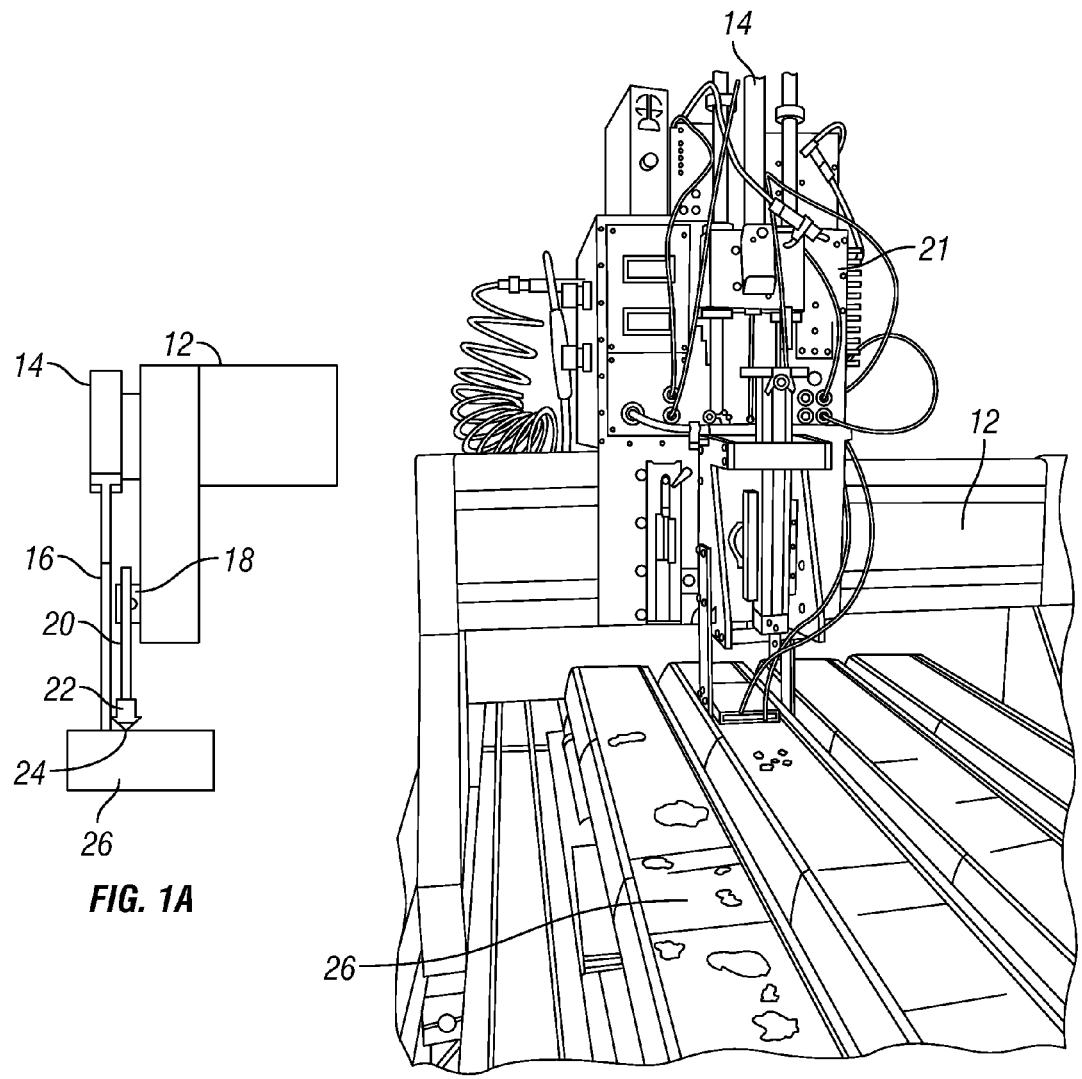
FIG. 1A and FIG. 1B show a schematic representation of a force-time impact measuring device according to the present disclosure. (Do we need to make FIGS. 1A and 1B correspond directly to one another? FIG. 1A is a simplification of what we implemented in 1B with regard to lifting and releasing the sensor).

An automated device for measuring mechanical properties of a material (such as elastic stiffness and mechanical strength) at a controlled location on the surface of a sample may be better understood with reference to FIG. 1A and FIG. 1B.

FIG. 1A shows the functional elements of the device in schematic form. A positioning system 12 may move the measurement components to a selected position in the X, Y (horizontal) plane of the device, e.g., slip rod 20, with mass 22 and instrumented probe tip 24 attached at a lower end thereof. The slip rod 20 may be slideably disposed within a linear bearing 18, and have a pincher or jaws (not shown in FIG. 1A) to selectively release the slip rod to be accelerated by gravity into a material sample 26. The slip rod 20, linear bearing 18, and a support rod 16 may be functionally coupled to a lift cylinder 14. The lift cylinder 14 may be raised to lift a frame (14A in FIG. 3A) and lowered when the frame and probe tip 24 are in the correct position for making a measurement. The jaws (not shown in FIG. 1) may hold the slip rod 20 in place for subsequent release so that the probe tip 24 accelerates toward the sample. FIG. 1B shows the system pictorially.

Figure 2:
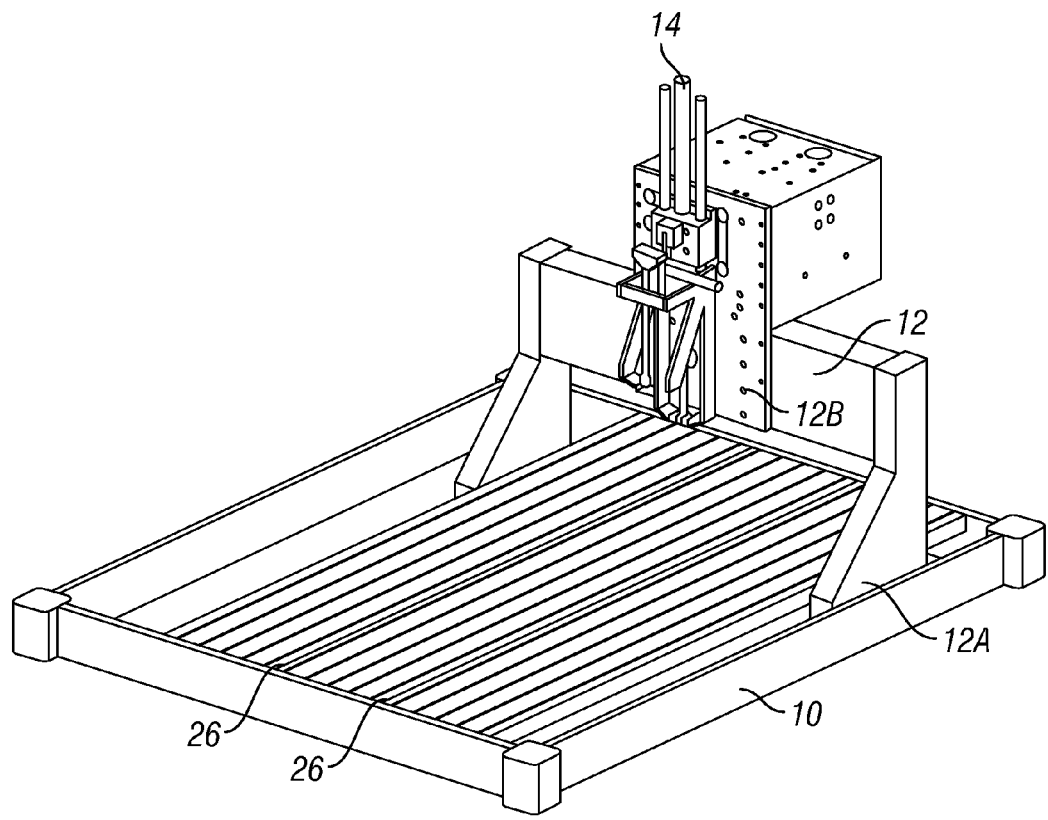
FIG. 2 shows the device of FIG. 1B in a sample holding frame.

FIG. 2 shows an oblique view of the system including the X-Y positioning system 12 with associated position sensors 12A, 12B mounted in a frame 10. The position sensors may be any type known in the art including proximity sensors, linear variable differential transformers or rotary encoders. The frame 10 may be configured to hold any selected number of samples 26 of material to be examined.

Figure 3B:
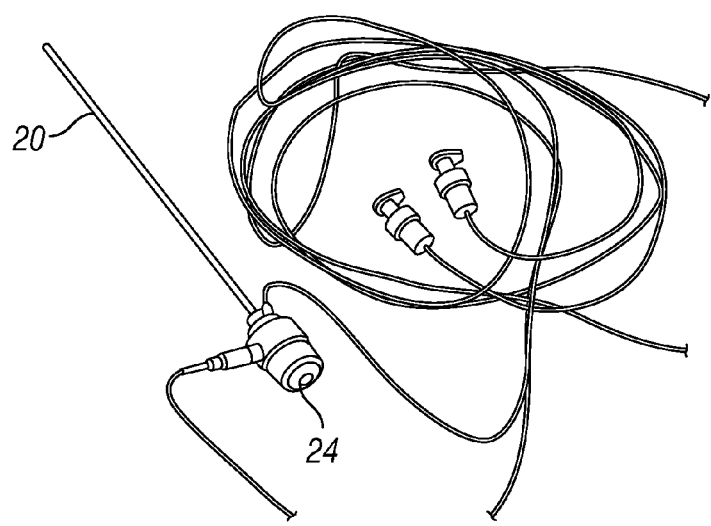
FIG. 3B shows an example probe tip having an accelerometer and force measuring sensor such as a strain gauge.
Figure 3A:
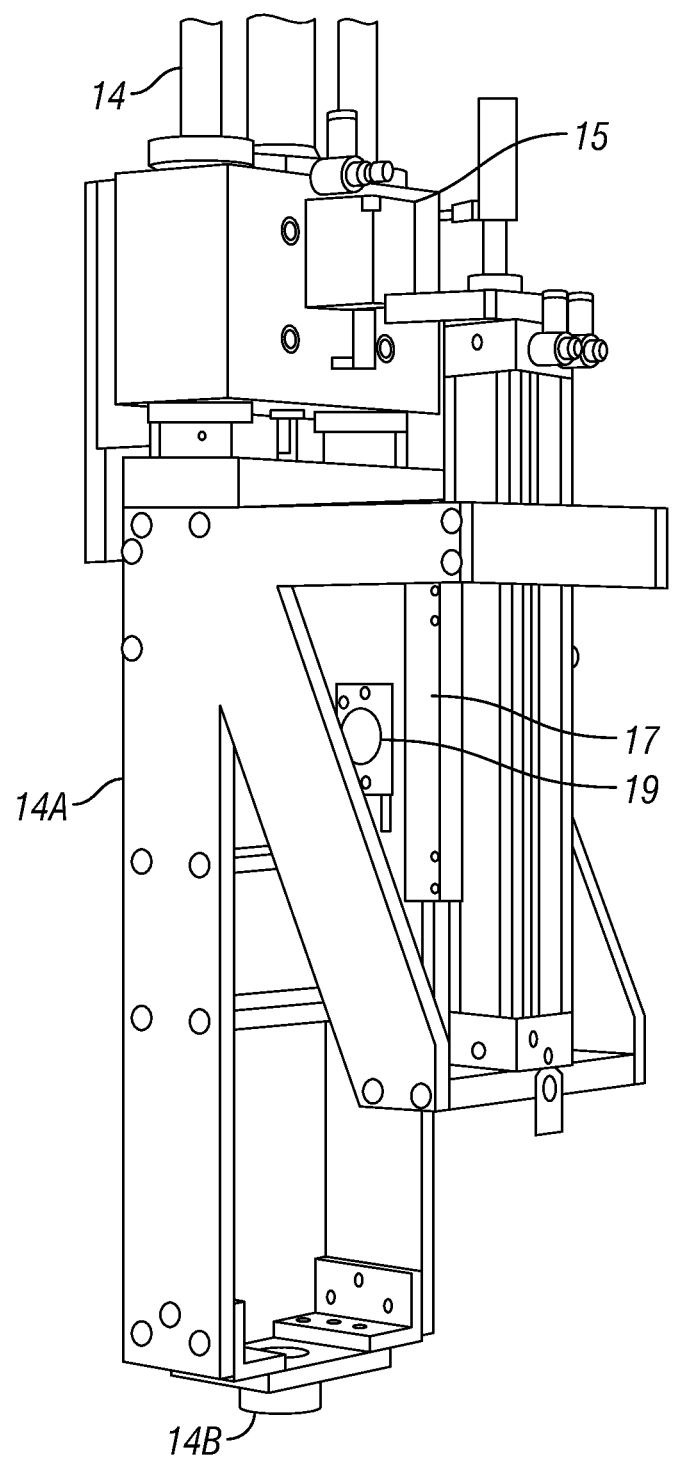
FIG. 3A shows a view of an impact hammer frame and impact hammer.

The measurement portion of the system is shown in more detail in FIG. 3A. A grip arm 17 and pneumatic jaws 19 may lift and hold the slip rod (20 in FIG. 1) in position until it is time to drop the slip rod (20 in FIG. 1). The foregoing components as well as the lift cylinder 14 may be disposed in a frame 14A. The frame 14A may include a rubber bumper or disc 14B on a bottom thereof to hold the sample from moving during the measurement and avoid damaging samples as the frame 14A is lowered into position for an impact experiment. FIG. 3B shows an example probe tip 24 coupled to the slip rod 20. The probe tip 24 may include an accelerometer and a force measuring gauge such as a resistance-type strain gauge. An example sensing device that may be used in some embodiments is known commercially as an "impedance head." A non limiting example of impedance head is sold commercially under model number 5860B by Dytran Instruments, Inc. 21592 Marilla Street, Chatsworth, Calif. 91311.

Signals from the X-Y position sensors (12A, 12B in FIG. 2) and the probe tip 24 sensors may be recorded by a processor (21 in FIG. 1) for analysis as will be explained below. The processor may also control movement of the X-Y positioning system, which may use as motive force motors with friction wheels, motors with worm gears, hydraulic cylinders or any other device known in the art for imparting precisely controllable movement within the two directions in a plane.

By making multiple measurements at various locations, the spatial variation in stiffness and mechanical properties can be quantified. This information can be used to predict the mechanical properties of the material when subjected to different boundary conditions, such as the prediction of the material behavior at a larger scale (e.g. the borehole scale) and/or the prediction of the material behavior when subjected to different stress conditions. The same information can also be used to classify mechanical subtypes within a sample, used either alone or in conjunction with other measurement devices mounted to the same platform.

Figure 4:
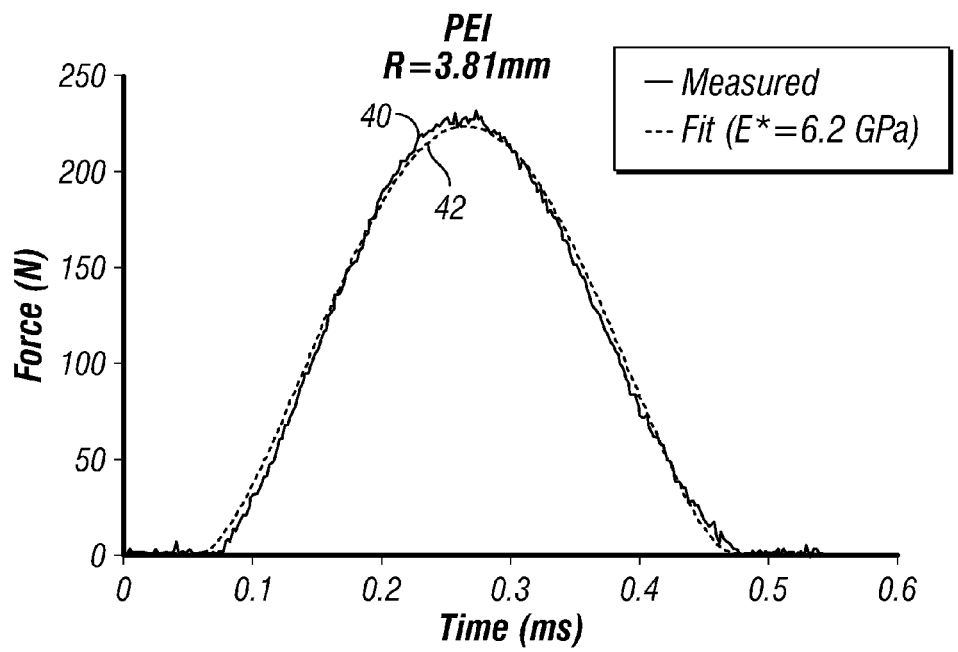
FIG. 4 shows an example force time curve generated using the device of FIG. 1B using a sample of polyetherimide (PEI) plastic and a predicted force time curve using known mechanical properties of PEI plastic.

Some elements of the example device according to the present disclosure may include:

(a) the capability to measure the force-time function of the impact of the probe tip with a sample of material to be tested. The force-time function of the impact can be analyzed in the context of a physical model to determine the mechanical properties of the material, such as its elastic stiffness. An example measurement and its interpretation in the context of elastic impact is shown in FIG. 4;

(b) the ability to measure the acceleration of the measurement device to provide a trigger signal for data acquisition and/or to provide more information concerning the physical details of the impact;

(c) the ability to automate the measurements, either repeatedly at a single location, or sequentially at multiple locations;

(d) the ability to firmly hold the sample onto the table, thus keeping the sample from moving when the measurement is made; and (e) the ability to precisely locate the device on the sample so that measurements can be made: at a particular location, repeatedly at the same spot, and/or repeatedly at the same spot after changing adjustable parameters of the device such as the tip geometry, the velocity of the impact, or the mass used for the measurement and repeatedly in a pattern such as a linear profile or a grid in order to quantify spatial variations. In mechanical properties of the material being tested.

The device may also have the capability to change the tip that impacts the sample in order to change the physical parameters of the measurement. In some uses of the device, measurements may be made on the same material at the same or similar position using different tips (24 in FIG. 1) each with a different geometry or physical properties. As an example, by comparing the results of the measurements using multiple tips each with different geometries and/or different selected physical properties, additional information about the mechanical properties of the material can be determined than can be determined using only one tip. In one example, the tip may be made from hardened stainless steel. In another example, the tip may be made from tungsten carbide. The foregoing are only example and are not intended to limit the scope of materials that may be used for the tip.

In one use of the device, measurements may be made using tips each having a different curvature and the results may be used to determine if the response of the material is consistent with the modeled elastic impact. If the results are consistent with predictions of elastic impact, it can be concluded that the mechanical strength of the material has not been exceeded and that the elastic stiffness of the material can be determined from the results. If the results are inconsistent with elastic property predictions, it can be concluded that damage has occurred as a result of the measurement, and thus the mechanical strength or elastic yield point of the material has been exceeded. Each of these observations may be used alone to place constraints on the mechanical strength of the material. Both of these observations made in combination may be used to further constrain the mechanical properties of the material, including its elastic stiffness and/or placing limits on its strength.

The device may also have the capability to change other attributes of the measurement, such as the velocity of the impact (e.g., by setting the drop height) and/or the mass of the impacting device, and/or as explained above the material properties of the impact tip. The observed changes in response of the material sample to the changes in mass or velocity used in the measurement can be used to better determine the properties of the material in the same or similar way to the observed changes due to changes in tip geometry as described above (e.g. to check for consistency and/or breakdown with the predictions of the response predicted by elastic theory). In one version of the invention, the velocity of impact is controlled by controlling the height from which the sensor head is dropped.

The device measurement may provide the ability to characterize the strength of a material and/or the relative strengths of two different materials.

FIG. 4 shows a graph of the measured force time function, at curve 40 of an impact on polyetherimide (PEI) plastic using the device, compared with a fit to a model at curve 42. Because the modeled force time function curve and measured force time function curve show good agreement, the elastic stiffness E* can be directly related to the elastic stiffness of the sample.

Figure 5:
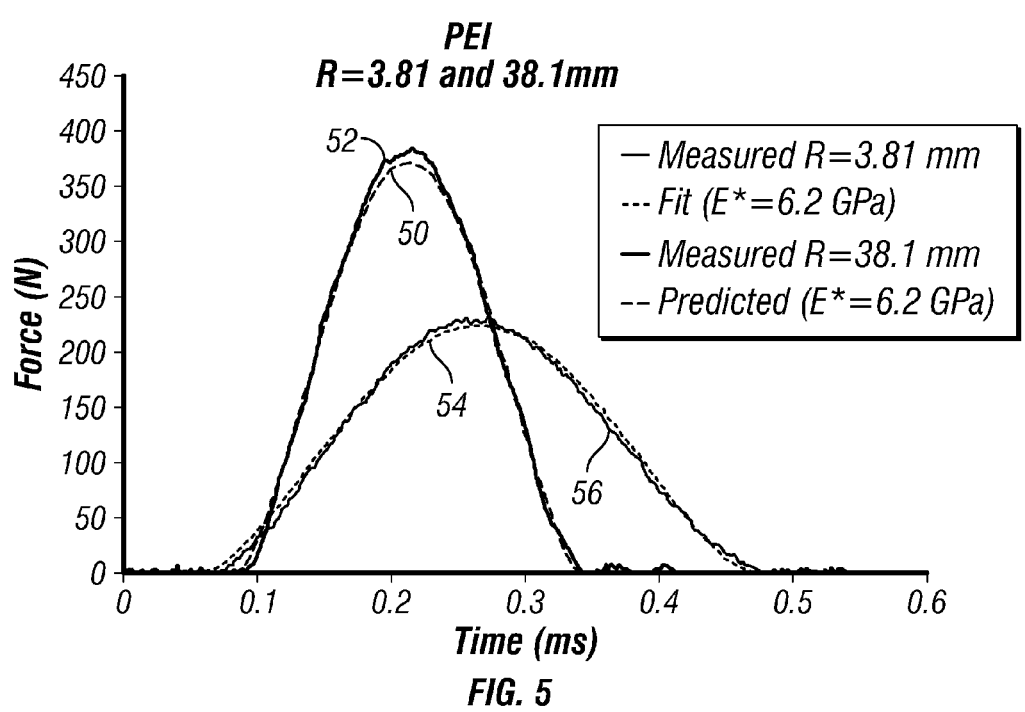
FIG. 5 shows predicted and measured force time curves for PEI plastic using two different radius probe tips on the device of FIG. 1B.

FIG. 5 shows graphs of an example of the use of two measurements made on the same material (PEI) using different tip geometry for each test. A initial measurement, curve 50 was made using a tip radius of 3.81 mm and the data was fit to a model, curve 52, that resulted in a prediction of the mechanical stiffness of the sample. The predicted stiffness of the material was used to predict the response to an impact using a tip of a different geometry, at curve 54. A measurement was made using that different geometry, shown at curve 56. The agreement between the prediction and the measured value are used to confirm that the material is responding elastically and thus the material strength has not been exceeded.

Figure 6:
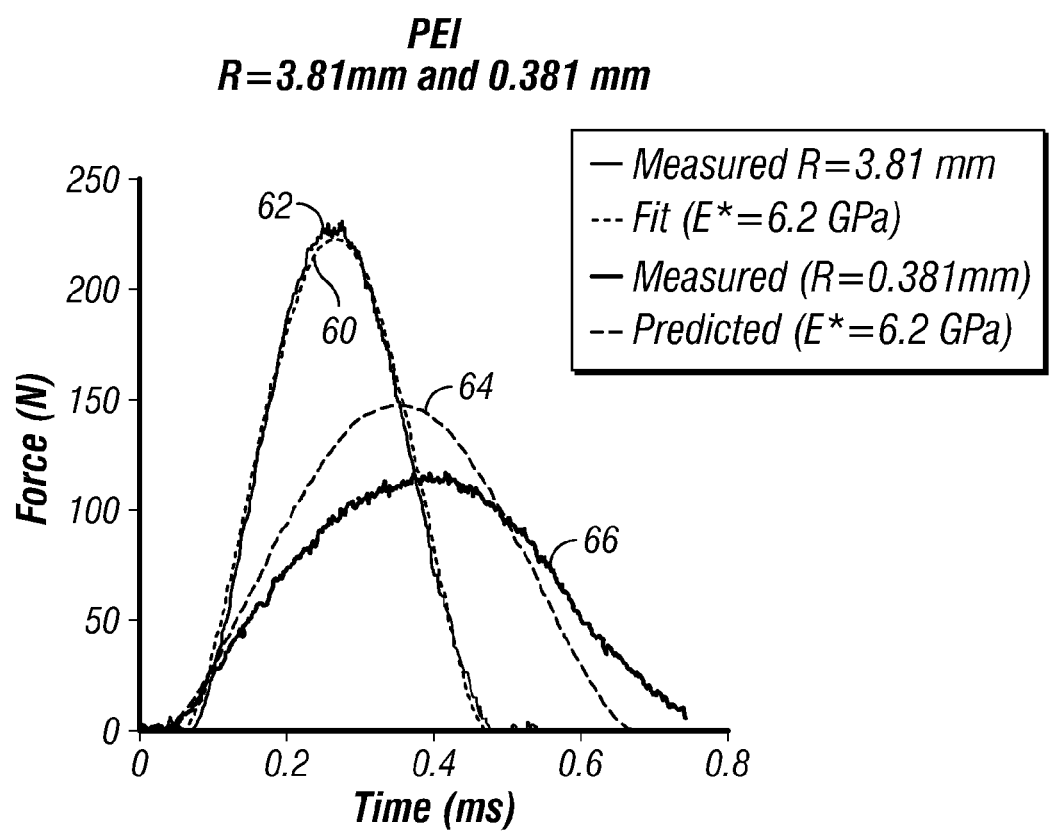
FIG. 6 shows similar graphs to FIG. 5, but where the measured force time curve for a tip of smaller radius indicates the elastic limit of the sample has been exceeded.

FIG. 6 shows an example of the use of the device to make two measurements on the same material (PEI) using different tip geometry. A initial measurement was made using a tip radius of 3.81 mm, at curve 60, and the data was fit to a model at curve 62 that resulted in a prediction of the mechanical stiffness of the sample. The predicted stiffness of the material was used to predict the response to an impact at curve 64 using a tip of a different geometry, in this case for a tip with smaller radius. A measurement was made using that different geometry as shown at curve 66. The lack of agreement between the prediction at 64 and the measured value of the force time curve at 66 were used to confirm that the material is responding inelastically to the impact by the tip of smaller radius and thus the material strength has been exceeded. For cases where damage occurs, the force above which the measured data deviates from the predicted value can be related to the strength of the material.

Figure 7A:
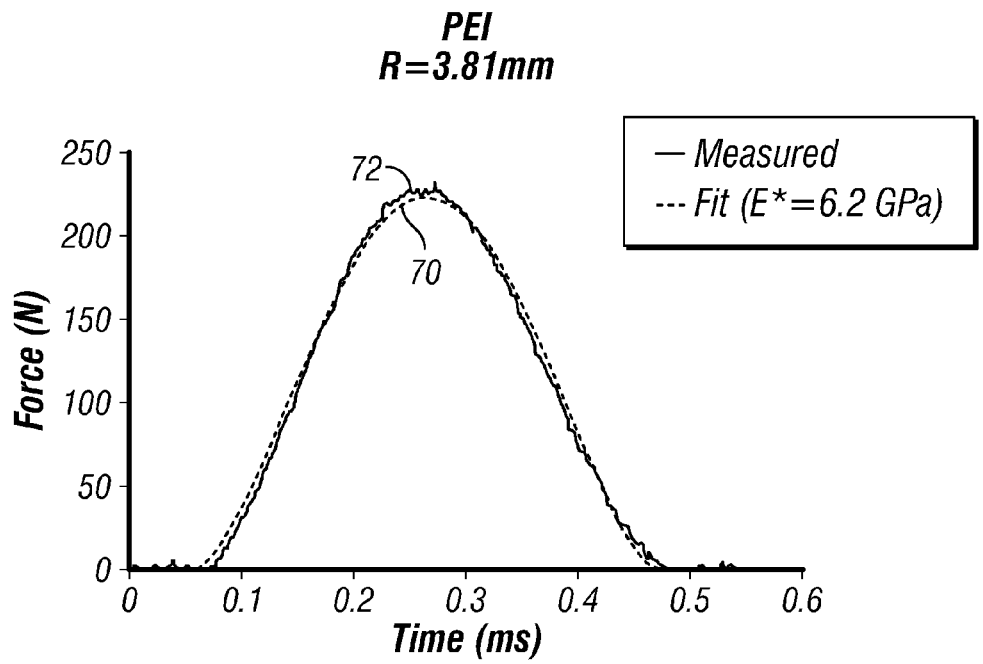
FIG. 7A shows measured and modeled force time curves for PEI plastic.
Figure 7B:
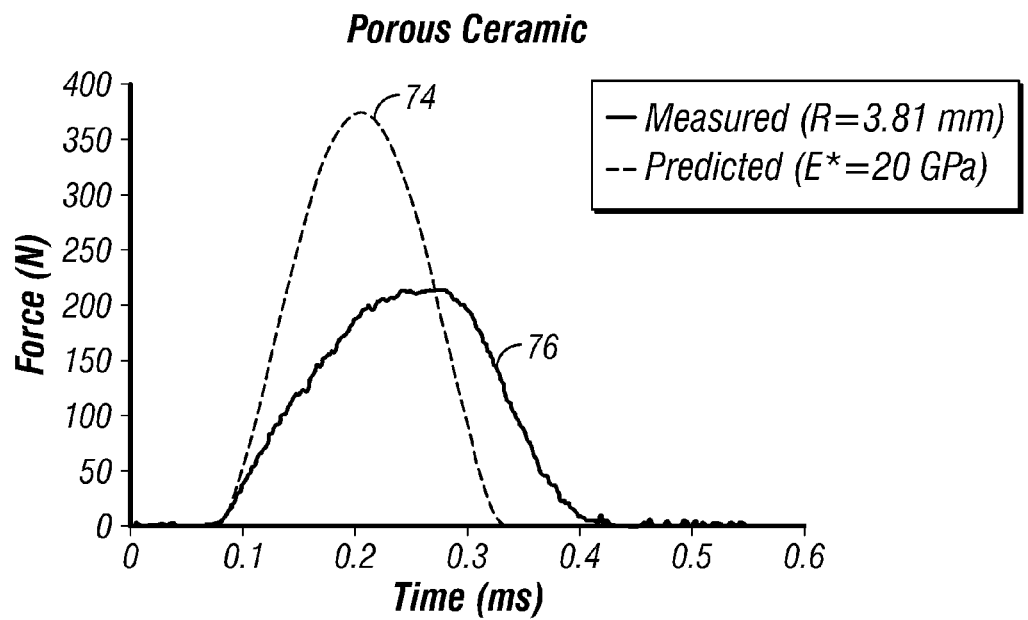
FIG. 7B shows a modeled force time curve for porous ceramic material and its corresponding measured force time curve.

FIGS. 7A and 7B show, respectively, examples of measurements on two different materials using the same measurement parameters. The predictions of the elastic response for the two materials based on the known material properties of those materials is shown for comparison. In FIG. 7A the impact on the PEI plastic as measured at curve 72 may be observed to fit elastic theory, as shown at curve 70 and no visual evidence of damage is observed, providing a lower limit constraint on its strength. In FIG. 7B, the force time function, impact curve 76, on a porous ceramic sample deviates from modeled elastic response at curve 74 indicating that damage occurs during impact. Clear visual evidence of damage to the porous ceramic sample was observed. For cases where damage occurs, the force above which the measured data deviates from the predicted value can be related to the strength of the material. The comparison of the two different responses may provide a comparison of mechanical properties of the two materials.

Example implementations of the device may include the ability to record, store, plot, present, and analyze the results as they are collected so that the measurements can be interpreted immediately or stored by a recording device for analysis at a later time.

Some example uses of the device may also include making measurements on core plug samples, thus providing information on the stiffness and/or strength of the cores without damaging the cores. In another example use of the device, the samples are rock cores of irregular geometry, such as a slabbed core sample, and the measurements are made as a function of position on the slabbed surface of the sample to quantify the variation in mechanical properties as a function of position such as depth from within the earth.

In another example use of the device, the force time measurements may be combined with measurements from other measurement probes to discover and quantify relationships between different properties and/or to provide the basis for a classification of physical subtypes within the sample. As one non-limiting example, the results from force time measurements made at selected distances (e.g., every 2 mm) along the length of a formation core sample may be analyzed along with other physical property measurements such as FTIR (Fourier transform infrared spectroscopy) spectral reflection data and acoustic velocity data. The combined measurements may be used to identify section of the core sample that are physically similar, and to relate mechanical properties to those sections. This type of information can be used to constrain physical models of the sub-surface, such as for the engineering of hydrocarbon reservoirs.

Figure 8:
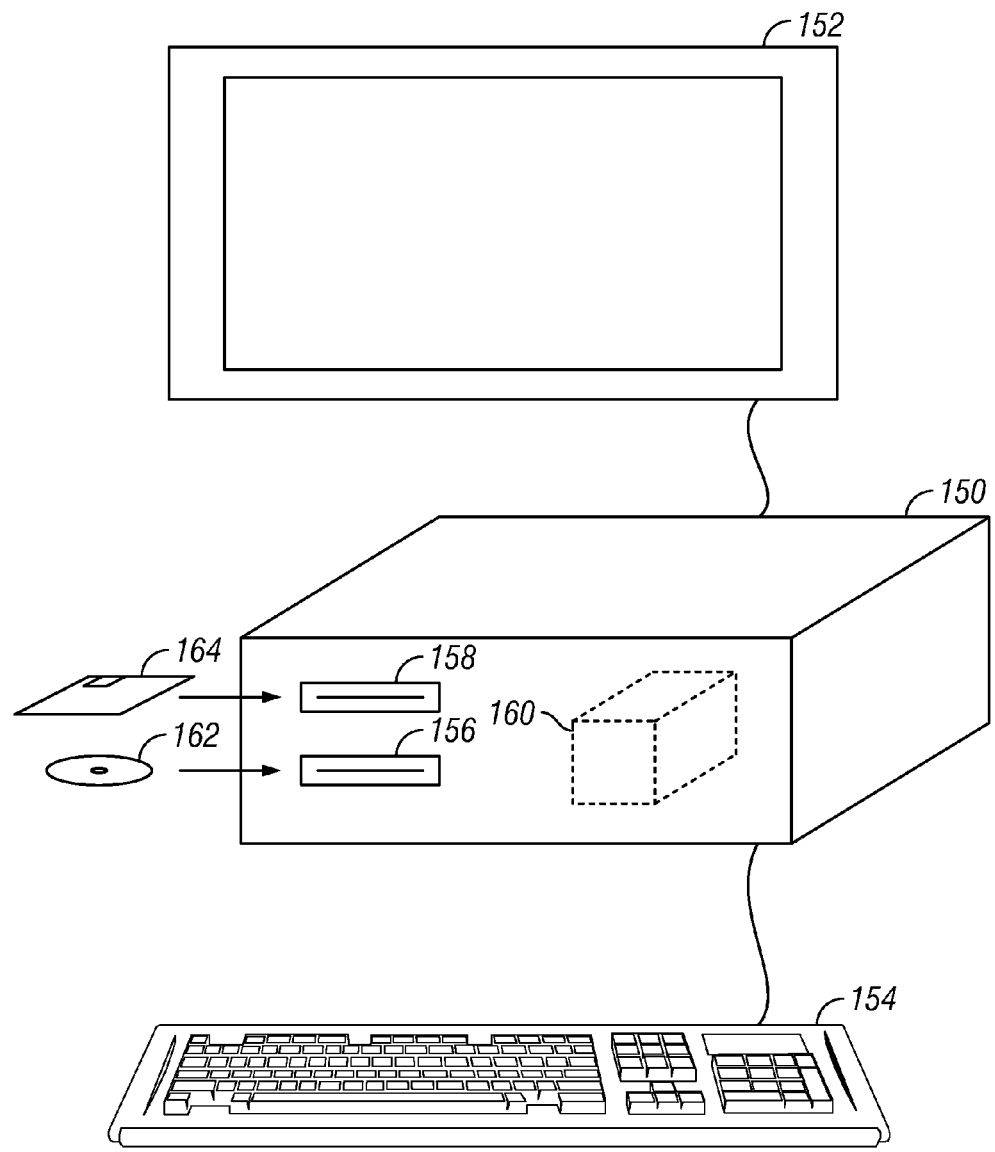
FIG. 8 shows an example computer that may be used in some examples.

Referring to FIG. 8, the foregoing process as explained with reference to FIGS. 1-7A and 7B, can be embodied in computer-readable code. The code can be stored on a non-transitory computer readable medium, such as solid state memory card 164, CD-ROM 162 or a magnetic (or other type) hard drive 166 forming part of a general purpose programmable computer. The computer, may be in signal communication with the processor (21 in FIG. 1B) to process acquired and recorded signals from the probe tip and the X-Y positioning system sensors (12A, 12B in FIG. 2).

The computer, as known in the art, may include a central processing unit 150, a user input device such as a keyboard 154 and a user display 152 such as a flat panel LCD display or cathode ray tube display. According to this aspect of the disclosure, the computer readable medium includes logic operable to cause the computer to execute acts as set forth above and explained with respect to the previous figures. The computer or parts thereof may be in the processor (21 in FIG. 1B or may be any other computer.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A method for determining mechanical properties of a material, comprising:
   positioning a probe tip of selected material properties having a selected geometry and a selected accelerating mass at a selected position and a selected height above a sample of the material;
   releasing the probe tip to accelerate toward the sample;
   measuring a first parameter comprising at least one of force and acceleration on the probe tip with respect to time;
   in a computer, using the measured first parameter with respect to time to determine a relationship of force applied by the probe tip to the sample with respect to time; and
   in the computer, using the determined relationship to determine at least one mechanical property of the material.

2. The method of claim 1 further comprising:
   repeating the positioning and releasing the probe tip wherein at least one of a selected radius of the probe tip, the selected accelerating mass, the selected position and the selected height are changed;
   measuring a second parameter comprising at least one of force and acceleration on the probe tip with respect to time;
   in the computer, using the measured second parameter to determine a second relationship of force applied by the probe top with respect to time; and
   in the computer comparing the first and second determined relationships to determine at least one mechanical property of the material.

3. The method of claim 1 further comprising comparing in the computer the first parameter related to force with respect to time to an expected relationship of force with respect to time for the material and determining if a strength of the material has been exceeded.

4. The method of claim 1 wherein the parameter related to acceleration is measured by an accelerometer proximate the probe tip.

5. The method of claim 1 wherein the parameter related to force is measured by a strain gauge.

6. The method of claim 1 further comprising moving the probe tip to a different selected position above the sample and repeating the releasing the probe tip and recording the first parameter with respect to time to determine spatial variation in mechanical properties of the sample.

7. The method of claim 1 further comprising comparing the at least one mechanical property with at least one of a Fourier transform infrared reflection spectrogram and an acoustic velocity to characterize the sample.

8. The method of claim 7 further comprising moving the probe tip to selected positions above the sample and repeating the dropping the probe and determining at least one mechanical property at each of the selected positions, and repeating the comparing with at least one of a Fourier transform infrared reflection spectrogram and an acoustic velocity to characterize a spatial distribution of mechanical properties of the sample.

9. The method of claim 1 wherein accelerating the probe tip comprises releasing the probe tip to free fall toward the sample.

10. A method for determining mechanical properties of a material, comprising:
   positioning a probe tip of selected material properties having a selected geometry and a selected accelerating mass at a selected position and a selected height above a sample of the material;
   releasing the probe tip to accelerate toward the sample;
   measuring a first parameter related to force on the probe tip with respect to time; and
   in a computer, using the measured first parameter with respect to time to determine at least one mechanical property of the material.

11. The method of claim 10 further comprising:
   repeating the positioning and releasing the probe tip wherein at least one of a selected radius of the probe tip, the selected accelerating mass, the selected position and the selected height are changed;
   measuring a second parameter related to force on the probe tip with respect to time; and
   in the computer, using the measured second parameter to determine at least one mechanical property of the material.

12. The method of claim 10 further comprising comparing in the computer the first parameter related to force with respect to time to an expected relationship of force with respect to time for the material and determining if a strength of the material has been exceeded.

13. The method of claim 10 wherein the parameter related to force is measured by a strain gauge.

14. The method of claim 10 further comprising moving the probe tip to a different selected position above the sample and repeating the releasing the probe tip and recording the first parameter with respect to time to determine spatial variation in mechanical properties of the sample.

15. The method of claim 10 further comprising comparing the at least one mechanical property with at least one of a Fourier transform infrared reflection spectrogram and an acoustic velocity to characterize the sample.

16. The method of claim 15 further comprising moving the probe tip to selected positions above the sample and repeating the dropping the probe and determining at least one mechanical property at each of the selected positions, and repeating the comparing with at least one of a Fourier transform infrared reflection spectrogram and an acoustic velocity to characterize a spatial distribution of mechanical properties of the sample.

17. The method of claim 10 wherein accelerating the probe tip comprises releasing the probe tip to free fall toward the sample.

* * * * *